United States Patent [19]

Foulletier

[11] Patent Number: 4,474,895
[45] Date of Patent: Oct. 2, 1984

[54] CATALYSTS FOR GASEOUS PHASE FLUORINATION OF ALIPHATIC CHLORINATED AND CHLOROFLUORINATED HYDROCARBONS

[75] Inventor: Louis Foulletier, Oullins, France

[73] Assignee: PCUK Produits Chimiques Ugine Kuhlmann, Courbevoie, France

[21] Appl. No.: 324,414

[22] Filed: Nov. 24, 1981

[30] Foreign Application Priority Data

Dec. 29, 1980 [FR] France .................. 80 27661

[51] Int. Cl.$^3$ .................. B01J 23/26; B01J 27/12; B01J 35/10; C07C 17/00
[52] U.S. Cl. .................. 502/181; 502/182; 570/165; 570/168
[58] Field of Search .............. 252/447, 441; 502/181, 502/182

[56] References Cited

U.S. PATENT DOCUMENTS

| | | | |
|---|---|---|---|
| 2,458,551 | 1/1949 | Benning et al. | 570/168 |
| 3,157,707 | 11/1964 | Clark et al. | 252/467 |
| 3,600,450 | 8/1971 | Kaess et al. | 260/653.3 |
| 3,812,028 | 5/1974 | Wennerberg et al. | 252/447 |
| 4,155,881 | 5/1979 | Sullivan | 252/441 |

FOREIGN PATENT DOCUMENTS

| | | |
|---|---|---|
| 1369786 | 7/1964 | France . |
| 2111865 | 6/1972 | France . |
| 56-24050 | 3/1981 | Japan .................. 252/447 |
| 943627 | 12/1963 | United Kingdom . |
| 975498 | 11/1964 | United Kingdom . |
| 1369870 | 9/1974 | United Kingdom . |
| 1369869 | 10/1974 | United Kingdom . |

*Primary Examiner*—P. E. Konopka
*Attorney, Agent, or Firm*—Pennie & Edmonds

[57] ABSTRACT

This invention relates to improved catalysts for gaseous phase fluorination of aliphatic chlorinated and chlorofluorinated hydrocarbons by hydrofluoric acid. The catalysts are characterized by an active carbon support having a total specific surface area greater than about 1000 m$^2$/g but less than about 2000 m$^2$/g, a surface area of pores of 40 to 50 Å in radius above about 5 m$^2$/g but less than about 15 m$^2$/g, a surface area of pores greater than or equal to 250 Å in radius above about 2 m$^2$/g but less than about 6 m$^2$/g, which has been impregnated with an aqueous chromium trioxide solution and dried. This invention also relates to gaseous phase fluorination processes for chlorinated or chlorofluorinated derivatives utilizing these catalysts in fluidized bed reactors.

5 Claims, No Drawings

CATALYSTS FOR GASEOUS PHASE FLUORINATION OF ALIPHATIC CHLORINATED AND CHLOROFLUORINATED HYDROCARBONS

TECHNICAL FIELD

This invention relates to improved catalysts for gaseous phase fluorination of aliphatic chlorinated and chlorofluorinated hydrocarbons by hydrofluoric acid. The catalysts are characterized by a chromium oxide base deposited on an active carbon support.

This invention also relates to gaseous phase fluorination processes of chlorinated or chlorofluorinated derivatives utilizing these chromium oxide catalysts in fluidized bed reactors.

BACKGROUND ART

Various catalysts which substitute fluorine atoms for chlorine atoms have been proposed for use in gaseous phase reactions. Frequently, these catalysts are oxides or halides of chromium, aluminum, cobalt, iron, titanium, nickel, copper, palladium or zirconium; which may be supported on active carbon or alumina. U.S. Pat. No. 2,458,551, for example, describes catalysts having a chromium trifluoride base deposited on active carbon or calcium fluoride.

U.S. Pat. No. 3,258,500 discloses a non-supported anhydrous trivalent chromium oxide catalyst prepared by the reduction of chromium trioxide and subsequent heating of the reduced product at a temperature of 400°–600° C.

British Pat. No. 896,068 and U.S. Pat. No. 3,157,707 describe alumina-supported chromium oxide catalysts prepared by the reduction of chromium trioxide by hydrogen. The catalysts are useful in the preparation of fluorinated compounds such as trichlorotrifluoroethane, dichlorotetrafluoroethane from hexachloroethane.

U.S. Pat. No. 2,892,000 discloses the preparation of vinyl fluoride and 1,1-difluoroethane by reacting hydrogen fluoride with acetylene in the presence of a catalyst comprising chromium oxide or chromium salt.

Other patents such as Japanese Application Nos. 70.116696 and 74.131610, teach the reduction of chromium trioxide by aldehydes or hydrazine, for the preparation of catalysts.

These commonly used chromium halide catalysts deposited on carbon supports are basically suitable for gaseous phase fluorination of chloroalkanes or chlorofluoroalkanes in fixed bed reactor systems. In fluidized bed reactors, which require regular-shaped particles and homogeneous granulometry, the prior art catalysts are inadequate and inefficient for use in fluorination processes. Simple grinding of the catalysts, followed by sifting for the selection of suitable-sized particles provides irregularly-shaped grains which are not suitable for use in fluidized bed reactors. Consequently, their use leads to a significant loss of the catalyst, which necessitates recharging the reactor at various intervals during the process.

The prior art catalysts often demonstrate at least one of the following disadvantages:
- low rate of conversion of hydrofluoric acid
- low productivity
- low selectivity
- a high level of asymmetric isomers in the production of trichlorotrifluoroethane and dichlorotetrafluoroethane.

SUMMARY OF THE INVENTION

This invention discloses gaseous phase fluorination catalysts for chlorinated and chlorofluorinated aliphatic hydrocarbons. The supported catalysts comprise a chromium oxide base deposited on an active carbon support, and are characterized in that the active carbon support is impregnated with chromium trioxide ($CrO_3$), the major portion of which is reduced to chromium sesquioxide ($Cr_2O_3$) by the active carbon.

The catalysts are prepared by impregnating active carbon, having a total specific surface area greater than about 1000 $m^2/g$ but less than about 2000 $m^2/g$, and a high mesoporosity and a macroporosity, with an aqueous solution of chromium trioxide. The catalyst is then dried at a temperature of approximately 150° C. Preferably, the catalyst comprises about 0.5 to 2.8 atoms/g of chromium per liter and is in the form of particles of about 100 μm to 3,000 μm in diameter.

The applicant has discovered that gaseous phase fluorination catalysts are frequently tainted by the formation of tar on their surfaces and that the use of gaseous phase fluorination catalysts in fluidized bed reactors is advantageous since they cause abrasion of the catalyst grains, thus eliminating any attached tar and promoting catalytic activity. The catalyst is uniquely consumed by attrition and there is no need to stop the reaction in order to recharge the reactor with the catalyst.

DETAILED DESCRIPTION OF THE INVENTION

The gaseous phase fluorination catalysts of this invention comprise an active carbon support having a total specific surface area greater than about 1000 $m^2/g$, but less than about 2000 $m^2/g$ which is impregnated with an aqueous solution of chromium trioxide and subsequently dried at a temperature of, advantageously, about 150° C.

The mesoporosity of the carbon support, defined by a surface area of pores of 40 to 50 Å in radius, should be greater than about 5 $m^2/g$ but less than about 15 $m^2/g$. The macroporosity of the support, defined by a surface area of pores equal to or above 250 Å in radius, should be greater than about 2 $m^2/g$ but less than about 6 $m^2/g$. These values are critical for obtaining high conversion rates of hydrofluoric acid.

A major portion of the chromium trioxide ($CrO_3$) used to impregnate the carbon support is reduced in the finished catalyst to chromium sesquioxide ($Cr_2O_3$) by the active carbon itself, without the use of any specific reducing agent. Although the reaction is highly exothermic, it can be easily controlled, even on a large scale. The reduction of chromium trioxide by the active carbon advantageously increases the macroporosity of the carbon support.

The catalysts of this invention can be used as they are after drying. Alternatively, at the end of the drying stage, the catalysts may be subjected to activation by hydrofluoric acid. This causes the formation of a small amount of chromium trifluoride on the surface of the catalyst grains.

The catalysts disclosed by this invention are particularly suitable for gaseous phase fluorination of chlorinated or chlorofluorinated derivatives of methane and ethane. These catalysts are less suitable for the fluorination of halogenated derivatives, ketones, such as hexachloroacetone, or nitriles, such as trichloroacetonitrile.

EXAMPLES

The following examples demonstrate various methods of preparing the catalysts of this invention and uses of the catalysts in various fluorination reactions. The examples are set forth for the purpose of illustration only and are not to be construed as limiting the scope of the invention in any manner.

EXAMPLE 1

A solution of 1.0 mole of chromium trioxide in 300 cm$^3$ of water is prepared. The solution is impregnated into 1 liter of active plant carbon having the following characteristics:
Density—0.586 g/cm$^3$
Granulometry—1.8 mm
Total Specific Surface Area—1,096 m$^2$/g
Surface Area of Pores Having a Radius ≦ 250 Å—2.16 m$^2$/g
Surface Area of Pores Having a Radius = 50–250 Å—16.42 m$^2$/g
Surface Area of Pores Having a Radius = 40–50 Å—8.01 m$^2$/g The active carbon adsorbs the entire solution. The catalyst is dried by air in a fluidized bed at a temperature of 150° C. Analysis of the dry catalyst shows that a major part of the chromium is present in the trivalent state.

The catalyst is advantageously used for the fluorination of trichlorotrifluoroethane in a fluidized bed under the following conditions:
Molar Ratio HF/C$_2$Cl$_3$F$_3$—1.11/1
Flow Rate—14.4 moles/h/l
Temperature—412° C.

The conversion rate of hydrofluoric acid is 71%. The conversion rates of trichlorotrifluoroethane are:
68% into dichlorotetrafluoroethane, containing 89% symmetric isomer
5% into monochloropentafluoroethane

EXAMPLE 2

Using the active carbon of Example 1, a catalyst containing 2.0 atoms/g of chromium per liter is prepared under similar conditions. The catalyst is used for the fluorination of trichlorotrifluoroethane in a fluidized bed under conditions similar to those of Example 1.

The conversion rate of hydrofluoric acid is 83%. The conversion rates of trichlorotrifluoroethane are:
72% into dichlorotetrafluoroethane, containing 82% symmetric isomer
10% into monochloropentafluoroethane

EXAMPLE 3

(Comparative Example)

A catalyst containing 1 atom/g of chromium per liter is prepared as in Example 1, but the active carbon support does not have the desired characteristics of mesoporosity and macroporosity. As the data below demonstrates, the support is not suitable for the preparation of the catalysts of this invention.

The active carbon used in this example has the following characteristics:
Density—0.659 g/cm$^3$
Total Specific Surface Area—1,347 m$^2$/g
Surface Area of Pores Having a Radius ≦ 250 Å—1.41 m$^2$/g
Surface Area of Pores Having a Radius = 50–250 Å—8.7 m$^2$/g
Surface Area of Pores Having a Radius = 40–50 Å—4.7 m$^2$/g This catalyst is used, under the conditions of Example 1, for the fluorination of trichlorotrifluoroethane in a fluidized bed.

The conversion rate of hydrofluoric acid is only 51%. The conversion rates of trichlorotrifluoroethane are:
63% into dichlorotetrafluoroethane, containing 78% symmetric isomer
2% into monochloropentafluoroethane

EXAMPLE 4

The catalyst of Example 2 is used in the fluorination of monochlorotrifluoromethane under the following conditions:
Molar Ratio HF/CF$_3$Cl—1.55/1
Contact Time—3.72 seconds
Temperature—450° C.

The conversion rate of hydrofluoric acid is 47%. The conversion rate of chlorotrifluoromethane into tetrafluoromethane is 73%.

By comparison, a catalyst prepared by impregnation of active carbon with chromium trifluoride, as demonstrated in U.S. Pat. No. 2,458,551, requires more demanding operating conditions:
Molar Ratio HF/CF$_3$Cl—3.1/1
Contact Time—12 seconds
Temperature—880° C.

The rate of conversion of hydrofluoric acid is only 28%. The rate of conversion of CF$_3$Cl into CF$_4$ is 88.5%.

A catalyst of this type has an extremely short life since it does not easily withstand temperatures above 500° C.

EXAMPLE 5

A catalyst similar to that in Example 1 is prepared, but it contains 2.5 atoms/g of chromium per liter. After the drying stage, it is activated by a hydrofluoric acid treatment carried out at 150° C. for 3 hours.

The catalyst is used for the fluorination of dichlorodifluoromethane in a continuous operation comprising two fluidized bed reactors mounted in series.

The first reactor, maintained at a temperature of 430° C., is fed with a mixture of 17.9 moles of hydrofluoric acid, 16.1 moles of chlorotrifluoromethane and 1.8 moles of recycled dichlorodifluoromethane. The contact time is 3 seconds.

The effluents of the first reactor are mixed with 11.0 moles of fresh dichlorodifluoromethane and sent into the second reactor, which is maintained at a temperature of 450° C. The contact time in the second reactor is 4 seconds. The effluents contain:
Trichlorofluoromethane (formed by dismutation)—1.2% in moles
Unreacted Dichlorodifluoromethane—6.2% in moles
Chlorotrifluoromethane—71.8% in moles
Tetrafluoromethane—20.8% in moles The total conversion rate of hydrofluoric acid is 94.9%. All of the tetrafluoromethane and part of the chlorotrifluoromethane are extracted from the operation, with the rest of the chlorotrifluoromethane being recycled to the first reactor. The unreacted dichlorodifluoromethane is recycled to the first reactor.

I claim:
1. A supported catalyst comprising a chromium oxide base deposited on an active carbon, wherein the active carbon is impregnated with aqueous chromium trioxide, the major portion of which is reduced to chromium sesquioxide by the active carbon and the active carbon comprises:
  (a) a specific surface area greater than about 1000 m$^2$/g but less than about 2000 m$^2$/g,
  (b) a surface area of pores of 40 to 50 Å in radius which is greater than about 5 m$^2$/g but less than about 15 m$^2$/g,
  (c) a surface area of pores equal to or above 250 Å in radius which is greater than about 2 m$^2$/g but less than about 6 m$^2$/g.

2. A catalyst according to claim 1, wherein the catalyst comprises about 0.5 to 2.8 atoms/g of chromium per liter.

3. A catalyst according to claim 2, wherein the catalyst is in the form of particles between about 100 μm to 3,000 μm in diameter.

4. A process for the preparation of a supported catalyst comprising active carbon having a chromium oxide base deposited on the active carbon comprising the steps of:
  (a) impregnating, by means of an aqueous chromium trioxide solution, an active carbon comprising:
    (1) a specific surface area greater than about 1000 m$^2$/g but less than about 2000 m$^2$/g;
    (2) a surface area of pores of 40 to 50 Å in radius which is greater than about 5 m$^2$/g but less than about 15 m$^2$/g;
    (3) a surface area of pores equal to or above 250 Å in radius which is greater than about 2 m$^2$/g but less than about 6 m$^2$/g; and
  (b) drying the impregnated carbon.

5. The process according to claim 4, wherein the catalyst is activated at the end of the drying stage by an anhydrous hydrofluoric acid treatment.

* * * * *